United States Patent [19]

Thornthwaite et al.

[11] Patent Number: 4,788,316

[45] Date of Patent: Nov. 29, 1988

[54] PREPARATION OF SULPHONATED AROMATIC ESTERS

[75] Inventors: David W. Thornthwaite, Neston; David W. Roberts, Bebington, both of Great Britain; Stephen A. Madison, Valley Cottage, N.Y.

[73] Assignee: Lever Brothers Company, New York, N.Y.

[21] Appl. No.: 942,564

[22] Filed: Dec. 16, 1986

[30] Foreign Application Priority Data

Dec. 20, 1985 [GB] United Kingdom ............... 8531392

[51] Int. Cl.$^4$ ............................................. C07C 143/38
[52] U.S. Cl. .................................. 558/268; 260/402; 558/271; 560/108; 560/142
[58] Field of Search ................ 260/402, 505 N; 560/142, 108; 558/271

[56] References Cited

U.S. PATENT DOCUMENTS

| | | | |
|---|---|---|---|
| 628,881 | 7/1899 | Wendt | 560/142 |
| 2,607,801 | 8/1952 | Milner | 260/505 N |
| 3,114,767 | 12/1963 | La Combe et al. | 260/486 |
| 3,116,321 | 12/1963 | Horn et al. | 260/470 |
| 4,403,087 | 9/1983 | Mark | 528/196 |
| 4,588,531 | 5/1986 | Balzer et al. | 260/402 |
| 4,588,532 | 5/1986 | Moyne et al. | 260/402 |
| 4,588,533 | 5/1986 | Berry, Jr. | 260/402 |
| 4,692,279 | 9/1987 | Nussbaum | 560/142 |

FOREIGN PATENT DOCUMENTS

| | | |
|---|---|---|
| 105672 | 4/1984 | European Pat. Off. . |
| 105673 | 4/1984 | European Pat. Off. . |
| 165480 | 12/1985 | European Pat. Off. . |
| 201222 | 12/1986 | European Pat. Off. . |
| 1496266 | 12/1977 | United Kingdom . |
| 1519351 | 7/1978 | United Kingdom . |

*Primary Examiner*—Michael L. Shippen
*Attorney, Agent, or Firm*—Milton L. Honig; James J. Farrell

[57] ABSTRACT

A process for preparing sulphonated aromatic esters of the group consisting of substituted or unsubstituted sulphonato-phenyl carboxylates and sulphonato-phenyl carbonates is disclosed, comprising the steps of:

(1) preparing the unsulphonated aromatic ester;
(2) sulphonating said unsulphonated aromatic ester; and
(3) neutralizing the acid-sulphonated aromatic ester in a non-aqueous organic solvent with an alkali metal, earth alkali metal or ammonium carboxylate in an amount in excess over the amount needed to neutralize the sulphonic acid group(s) and any free or complexed $SO_3$ present in the product mixture from the sulphonation reaction.

Preferred neutralizing agent is sodium acetate; preferred solvents are acetic acid or glyme and diglyme.

13 Claims, No Drawings

PREPARATION OF SULPHONATED AROMATIC ESTERS

This invention relates to a method of preparing sulphonated aromatic esters and, in particular, to a method of preparing substituted or unsubstituted sulphophenyl carboxylates and carbonates.

Sulphophenol esters form a class of compounds which are known to be suitable for use in detergent compositions as so-called bleach activators. Owing to their reaction in aqueous solution with inorganic peroxygen bleaches, forming the much more effective organic peroxy acids, they have the ability to enhance the bleaching action at low temperatures ($<70°$ C.) of inorganic peroxygen bleaches normally included in detergent compositions such as perborate or percarbonate.

Conventionally, sulphophenol esters are prepared by acylating the corresponding phenol sulphonate salt with the appropriate acyl chloride, such as e.g. described in the British Patent Specification No. 1 519 351.

In the European Patent Applications Nos. 0 153 222 and 0 153 223 an acylating method is described involving the reaction of the phenol sulphonate with the appropriate acid anhydride in an aprotic solvent in the presence of a catalytic amount of a sulphonic acid or a salt of a $C_7$–$C_{12}$ carboxylic acid.

An alternative route involves a transesterification step to the appropriate acid anhydride and a subsequent or simultaneous reaction thereof with the phenol sulphonate salt. Examples of this route are described in the European Patent Applications Nos. 0 105 672 and 0 105 673.

Although prior art methods may result in suitable yields, they have several drawbacks in that they involve reaction steps under anhydrous conditions and of a heterogeneous nature (acylation reaction of the phenol sulphonate salt), which is undesirable both technically and economically. Generally, the reaction proceeds very slowly because of its heterogeneous nature and requires an excess of acylating agent and higher temperature to achieve satisfactory yields.

It has also been suggested to carry out the sulphonation of the aromatic ring only after the preparation of the unsulphonated ester, such as described in EP-A- 0165480.

The preparation of sulphonated aromatic esters, i.e. acyloxy benzene sulphonates, comprises the steps of
(1) providing the unsulphonated ester;
(2) sulphonating said unsulphonated ester; and thereafter
(3) neutralising the aromatic ester sulphonic acid with an aqueous solution of an inorganic base or with a solution or slurry of the inorganic base in an organic solvent.

Since it is known that activated phenol esters are easily hydrolysable compounds, the neutralisation in aqueous medium as practised in the art does not go without problems. Various precautions and measures should be taken to avoid hydrolysis of the ester group(s) in this step so as to obtain a satisfactory yield. Once hydrolysis of the ester group(s) takes place in the neutralising step, solvent extraction of the unreacted phenol ester is very difficult. The result thereof is that the method of the art only produces acyloxy benzene sulphonates at rather low yields. EP-A- 0140251 (BASF) proposes a method of neutralising acyloxy benzene sulphonic acid in aqueous medium under very specific conditions. Still, this method will not be sufficient to arrive at a satisfactorily high yield. A further drawback is that the method as proposed requires a very long reaction time of 3 to 10 hours, generally about 5 hours, and only when freeze-drying is applied, which is a very uneconomical process, to isolate the product from the aqueous solution, can satisfactory yields be obtained.

Previous investigators have also made attempts to neutralise acyloxy benzene sulphonic acids under nonaqueous conditions in various inert organic solvents using alkali carbonate, bicarbonate or acetate, but without much success. Protic solvents, e.g. low alcohols and glycols, have also been tried, but were found unsuitable as they cause transesterification.

It has now surprisingly been found that high yields of acyloxy benzene sulphonates can be obtained if the neutralisation is carried out in a non-aqueous organic solvent with an alkali metal, earth alkali metal or ammonium carboxylate in an amount in excess over the amount needed to neutralise the sulphonic acid group(s) and any free or complexed $SO_3$ present in the product mixture from the sulphonation reaction.

In a specific embodiment of the invention, and by way of illustration, the present invention contemplates an improved method of preparing a sulphonated aromatic ester of the general formula:

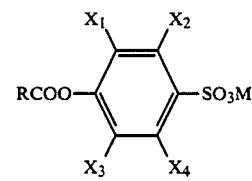

wherein R is a substituted or unsubstituted phenyl, $C_1$–$C_{18}$, preferably $C_2$–$C_{10}$ alkyl or alkoxyl radical, $X_1$ to $X_4$ are equal or different, and selected from the group of hydrogen, halogen, $C_1$–$C_4$ alkyl and $C_1$–$C_4$ alkoxyl radicals, and M is an alkali metal, an alkaline earth metal or an ammonium group; comprising the steps of (1) preparing the corresponding unsulphonated aromatic ester;
(2) sulphonating said unsulphonated ester; and
(3) neutralising said acid-sulphonated ester in a non-aqueous organic solvent with an alkali metal, earth alkali metal or ammonium carboxylate in an amount in excess over the amount needed to neutralise the sulphonic acid group(s) and any free or complexed $SO_3$ present in the product mixture from the sulphonation reaction.

In other embodiments, the invention contemplates the preparation of sulphonated aromatic esters of the general formula:

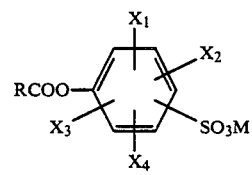

wherein R is as defined above; $X_1$–$X_4$ may be hydrogens, or one or more may be halogens, $C_1$–$C_4$ alkyl or alkoxyl radicals, RCOO-, or $SO_3M$; and M is as defined above, comprising the steps of:

(1) preparing the corresponding unsulphonated aromatic ester;

(2) sulphonating said unsulphonated aromatic ester; and (3) neutralising said acid-sulphonated aromatic ester in a non-aqueous organic solvent with an alkali metal, earth alkali metal or ammonium carboxylate in an amount in excess over the amount needed to neutralise the sulphonic acid group(s) and any free or complexed $SO_3$ present in the product mixture from the sulphonation reaction.

Accordingly, the invention provides a process for preparing sulphonated aromatic esters selected from the group of substituted or unsubstituted sulphonato-phenyl carboxylates and sulphonato-phenyl carbonates comprising the steps of:

(1) preparing the unsulphonated aromatic ester;

(2) sulphonating said unsulphonated aromatic ester; and (3) neutralising said acid-sulphonated aromatic ester in a non-aqueous organic solvent with an alkali metal, earth alkali metal or ammonium carboxylate in an amount in excess over the amount needed to neutralise the sulphonic acid group(s) and any free or complexed $SO_3$ present in the product mixture from the sulphonation reaction.

The first step of the method according to the present invention comprises the preparation of the unsulphonated aromatic ester. This step of the method can be carried out by any conventional route suitable for the preparation of esters. In general, the hydroxy aromatic starting material is the substituted or unsubstituted phenol, resorcinol, catechol or hydroquinone, which is subsequently reacted with the appropriate carboxylic acid or the anhydride or chloride thereof.

The reaction between the hydroxy aromatic compound and the appropriate carboxylic acid preferably is carried out in the presence of a p-toluene sulphonic acid catalyst under heating to about 110° C. and removal of the water formed. When the corresponding acid chloride is used, the reaction is carried out by mixing the hydroxy aromatic compound and the appropriate carboxylic acid chloride, and stirring the mixture at a temperature of 30–20 50° C., preferably 40° C., for a period of 1 to 2 hours.

In the second step of the method according to the present invention, the ester resulting from step 1 is sulphonated with a strong sulphonating agent such as sulphuric acid or sulphur trioxide.

Preferably sulphur trioxide is used in admixture with an inert gas such as nitrogen. In order to achieve hggh degrees of sulphonation, amounts of sulphur trioxide are used in excess of 1:1 stoichiometry with the aromatic ester. The molar excess of sulphur trioxide which must be used to achieve substantially complete sulphonation of the aromatic ester is dependent on the reactivity of the ester and the temperature. Preferably the mole ratio of sulphur trioxide to ester is within the range of up to 2.5:1, such as within the range of from 1.1:1 to 2.5:1. Reaction temperatures lie within the range of 0° to 150° C. and preferably 30° to 130° C.

Preferably, the ester/sulphur trioide reaction mixture is subjected to an aging step during which the sulphonation of the ester proceeds substantially to completion. The period of aging will reduce with the use of higher molar levels of sulphur trioxide in the reaction mixture.

An alternative sulphonation method involves the use of a carboxyl sulphonic acid as sulphonating agent. This sulphonating agent is preferably prepared in situ by mixing the carboxylic acid anhydride and sulphuric acid. To avoid transesterification problems it is of advantage to use the carboxylic anhydride corresponding to the carboxylic acid part of the unsulphonated aromatic ester. Alternatively, acetyl sulphonic acid can be used as sulphonating agent, though it may result in some transesterification of the initial unsulphonated aromatic ester.

The sulphonation reaction conditions may be steered such that more or less of di-sulphonated products are produced.

Subsequent to the sulphonation step, the resulting sulphonic acid is neutralised in a non-aqueous organic solvent with an alkali metal, ammonium or earth alkali metal carboxylate an amount in excess over the amount needed to neutralise the sulphonic acid group(s) and any free or complexed $SO_3$ present in the product mixture from the sulphonation reaction and subsequent vacuum removal of the acid. The alkali or ammonium carboxylate may be any carboxylate having a chain length corresponding to the RCOO-group, though alkali metal acetate, particularly sodium acetate, is preferred.

A preferred solvent is a carboxylic acid, particularly acetic acid.

Other preferred solvents are the lower $C_1$-$C_4$ alkyl ethers of ethylene glycol. especially ethylene glycol dimethyl ether (glyme) and diethylene glycol dimethyl ether (di-glyme).

Equally suitable solvents for use in the present invention are, for example, lower alcohols, such as methylated spirits; halogenated hydrocarbons, such as chloroform; and glycols.

The best condition for this neutralisation step is when the temperature during the neutralisation is kept as low as possible, but at such degree that the solvent is still in liquid form. For example, if acetic acid is used, the temperature should not reach below 17° C. as the acetic acid would solidify, whereas a temperature as low as 0° C. can be used if glyme is used as the solvent.

A surprising element of the present invention is that if the alkali metal carboxylate, e.g. sodium acetate, is used in excess over the amount needed to neutralise the sulphonic acid group(s) and any free or complexed $SO_3$ present in the product mixture from the sulphonation reaction, the risk of transesterification is minimised. The invention will now be illustrated in greater detail by way of examples.

EXAMPLE I

Phenol was acetylated with a 1.5 times molar excess of acetyl chloride at room temperature, the excess acetyl chloride being removed by evaporation under reduced pressure. A very high yield of phenyl acetate was produced. To this reaction product a 2.4 times molar excess of acetic anhydride was added with stirring, followed by a 1.5 times molar excess of sulphuric acid added dropwise at 50° C. over 30 minutes. After stirring for a further 60 minutes, the mixture was neutralised using a 1.5 time molar excess of sodium acetate in glacial acetic acid solution. Trituration of the reaction mixture with ether followed by filtration resulted in a dry yellow solid. This was recrystallised from methanol and washed with sodium carbonate solution. A 99% conversion to sodium sulphonatophenyl acetate was achieved.

COMPARATIVE EXAMPLE A

Phenol (19.2 g) was dissolved in dry dichloromethane (100 ml) and to this solution was added octanoyl chloride (32.5 g). The mixture was stirred for a period of one hour while hydrogen chloride gas was evolved.

The solution was checked by gas-liquid chromatography to ensure that the esterification was complete. Subsequently, the solution was transferred to a closed reaction vessel. Sulphur trioxide liquid (17.6 g) was added dropwise to a vaporizer under heating and continuous flushing with dry nitrogen at a flow rate of about 1.5-2 l/min, the outflowing mixture containing 8% $SO_3$ in nitrogen. This gas was then bubbled through the reactor vessel while the ester solution was continuously stirred and the temperature maintained between 30° and 40° C. After 45 minutes the contents of the reactor were poured into water while maintaining the pH between 6 and 7 with sodium hydroxide (circa 5M solution). The neutral solution was then freeze-dried, giving a yield, after recrystallisation from methanol, of 90% (58 g) of sodium sulphonato-phenyl octanoate. When the neutral solution was dried by other means than freeze-drying, a substantial drop in yield of sodium sulphonato-phenyl octanoate was observed.

EXAMPLE II

Procedure for manufacture of sodium octanoyloxy benzene sulphonate

Phenyl octanoate (42 g:0.18 M) [prepared by reacting phenol with octanoyl chloride or octanoic acid] was sulphonated in a stirred tank reactor (250 ml three-necked flask) using sulphur trioxide in nitrogen (7% dilution) at a mole ratio 1.5:1 at 30° C. for 1 hour. The acid mix in this case was neutralised between pH's 5-7 using sodium hydroxide. The resulting solution was freeze-dried and the solid residue extracted with methanol and filtered to remove inorganic material. The overall yield of product was 56 g (90%).

This experiment was repeated and the acid mix was split into two portions (20 g each; the remaining 16 g was stored). The first portion was neutralised between pH 6-7 with sodium carbonate solution and then concentrated under reduced pressure ca 50° C. The pasty solid was extracted with ether to give an oil identified as octanoic acid (9.5 g) and a white solid identified as phenol sulphonic acid sodium salt (12.5 g). Small amounts of product were detected, but at a very low level, which shows that hydrolysis occurs if the water is removed other than by freeze-drying.

The second portion (20 g) was added to glacial acetic acid (100 ml) which contained sodium acetate (5.5 g) and a white solid was precipitated by adding ether (500 ml). This solid was removed by filtration and dried in vacuo to give the desired product (20.5 g; 95%).

EXAMPLE III

A. Preparation of Alkyl Phenyl Carbonates

The starting alkyl phenyl carbonates were easily prepared and were obtained as subsequently described for hexyl phenyl carbonate. To a 500 ml three-necked flask equipped with a dropping funnel and mechanical stirrer were added 31.6 grams (0.40 mole) of pyridine, 20.4 grams (0.20 mole) of hexanol and 50 ml of diethyl ether. To this solution was then added dropwise 31.3 grams (0.20 mole) of phenyl chloroformate in 50 ml of diethyl ether. The reaction flask was cooled with an ice bath during the addition. Precipitation of salts occurred soon after addition was commenced. Upon completion of addition, an additional 50 ml of diethyl ether was added to facilitate stirring. The reaction mixture was allowed to warm to room temperature. At the end of four hours of stirring at room temperature, an aliquot of the reaction mixture was analyzed by infrared. No hexanol was indicated. The reaction mixture was then filtered and the solid washed twice with diethyl ether. All ether phases were combined and dried over magnesium sulphate. After removal of the dessicant and diethyl ether solvent, the residual liquid was fractionally distilled under reduced pressure through a short Vigreaux at 95° C. (75 microns). The yield was 39.7 grams (89%). The isobornyl, heptyl, cyclohexyl and ethyl phenyl carbonates were also prepared in comparable yields.

B. Sulphonation of the Alkyl Phenyl Carbonates

Liquid sulphur trioxide (1.1 equivalents) is added dropwise (approximately 1 drop/15 seconds) from an addition funnel to a heated 500 ml three-necked flask fitted with a magnetic stirrer. An oil bath maintained the flask temperature between 130° and 140° C. Nitrogen gas which was dried by passing through two sulphuric acid gas scrubbers (and one empty scrubber to contain any sulphuric acid mist) was continuously flushed through the vaporizer flask at a rate of 1.5-2.0 l/minute and served to sweep out the vaporizing sulphur trioxide. The reactor flask was connected to the vaporizer flask via a glass adapter and Teflon tubing and was equipped with a magnetic stirred, addition funnel and condenser topped with a calcium chloride drying tube. The reactor flask contained one equivalent of alkyl phenyl carbonate in $CH_2Cl_2$ (100 ml/0.2 mole carbonate) and was maintained between 40° and 50° C. (reflux temperature of methylene chloride) throughout the reaction. The gaseous sulphur trioxide came into the reactor vessel via a dispersion tube with the sintered end immersed in the solvent. During the sulphur trioxide addition, vigorous stirring was maintained in the reactor flask. Some sulphur trioxide, as well as methylene chloride, is lost during this phase of the reaction. Therefore, it is necessary to direct the escaping sulphur trioxide into a flask containing 0.1 N sodium hydroxide. Methylene chloride is replenished through the addition funnel on the reactor flask. After the addition was completed, heating and stirring were continued for an additional 45-60 minutes. The reaction solution is only lightly coloured at the end of this period.

C. Neutralisation of the Sulphonated Alkyl Phenyl Carbonates

Neutralisation of the reaction solution was effected by pouring it into a flask containing a solution of anhydrous sodium acetate (1.1 equivalents) and glyme (150 ml/0.2 mole alkyl phenyl carbonate). The solution was maintained at 0° C. and stirred continuously during neutralization. The sodium alkyl 4-sulphophenyl carbonate began to precipitate immediately. After 15 minutes of stirring, the glyme and acetic acid were removed under vacuum. The resultant white solid is washed twice with diethyl ether and recrystallised from methanol. Carbonate (% yield) prepared by this procedure included:

Sodium ethyl 4-sulphophenyl carbonate (84%)
Sodium heptyl 4-sulphophenyl carbonate (76%)
Sodium hexyl 4-sulphophenyl carbonate (90%).

Although the use of glyme is described, the neutralisation can also be performed with glacial acetic acid, or other suitable solvents such as chlorinated hydrocarbons.

EXAMPLE IV

Procedure for manufacture of sodium benzoyloxy benzene sulphonate

Phenyl benzoate (14.4 g; 0.07 M) [prepared by phenol with benzoyl chloride or benzoic acid] was sulphonated in dichloromethane (50 ml) by the addition of sulphur trioxide in a mole ratio of 1.1:1. This reaction was carried out at 35° C. over a period of 2 hours. The acid paste was obtained by removal of the solvent under reduced pressure and this paste was split into several portions.

The first portion (5 g) was dissolved in water (50 ml) and neutralised with sodium bicarbonate (1.66 g) and the water was removed under reduced pressure. The solid residue was triturated with ether and the while solid (35 g; 64.9%) was identified as the product by Hnmr and infrared and was found to be 73% pure.

The second portion (5 g) was added to industrial methylated spirits (40 ml) containing sodium acetate (1.62 g). A white product crystallised out of solution was separated by filtration and dried in vacuo (3.9 g; 72%). The material was analysed by Hnmr and infrared and was shown to be 81% pure.

The above examples show that esters can be sulphonated in good yield. They also show that neutralisation in non-aqueous solvents gives high purity products in good yields.

We claim:

1. A process for preparing substituted or unsubstituted sulphonato-phenyl carbonates having the general formula:

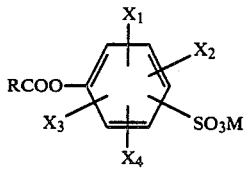

werein R is a $C_1$–$C_{18}$ normal alkoxyl radical; $X_1$–$X_4$ may be hydrogens, or one or more may be halogens, $C_1$–$C_4$ alkyl or alkoxyl radicals, RCOO— wherein R is defined as above, or $SO_3M$; and M is an alkali metal, earth alkali metal or ammonium group, comprising the steps of:
   (1) preparing the corresponding unsulphonated phenyl carbonate ester;
   (2) sulphonating said unsulphonated phenyl carbonate ester to form a sulphonic acid derivative; and
   (3) neutralising said sulphonic acid derivative of phenyl carbonate ester in a non-aqueous organic solvent with an alkali meal, earth alkali metal or ammonium carboxylate in an amount in excess over the amount needed to neutralise the sulphonic acid groups and any free or complexed $SO_3$ present in the product mixture from the sulphonation reaction.

2. A process according to claim 1, wherein said carboxylate used in the neutrailisation step is an alkali metal acetate.

3. A process according to claim 2, wherein said alkali metal acetate is sodium acetate.

4. A process according to claim 1, wherein said solvent is acetic acid.

5. A process according to claim 1, wherein said solvent is glyme (ethylene glycol dimethyl ether) or di-glyme (diethylene glycol dimethyl ether).

6. A process according to claim 1, wherein the neutralisation reaction is carried out as the lowest possible temperature whereby the solvent is still in liquid form.

7. A process for preparing substituted or unsubstituted sulphonatophenyl carbonates having the general formula:

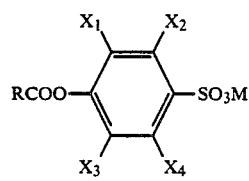

wherein R is a normal alkoxy radical having from 1 to 18 carbon atoms; $X_1$ to $X_4$ are equal or different, and selected from the group of hydrogen, halogen, $C_1$–$C_4$ alkyl and $C_1$–$C_4$ alkoxyl radicals, and M is an alkali metal, an alkaline earth metal or an ammonium group; comprising the steps of
   (b 1) preparing the corresponding unsulphonated phenyl carbonate ester;
   (2) sulphonating said unsulphonated phenyl carbonate ester to form a sulphonic acid derivative; and
   (3) neutralising said sulphonic acid derivative of phenyl carbonate ester in a·non-aqueous organic solvent with an alakli metal, earth alkali metal or ammonium carboxylate in an amount in excess over the amount needed to neutralise the sulphonic acid group and any free or complexed $SO_3$ present in the product mixture from the sulphonation reaction.

8. A process according to claim 7, wherein said solvent is acetic acid.

9. A process according to claim 7, wherein said solvent comprises a $C_1$-$C_4$ alkyl ether of ethylene glycol.

10. A process according to claim 9, wherein said solvent is glyme (ethylene glycol dimethyl ether) or di-glyme (diethylene glycol dimethyl ether).

11. A process according to claim 7, wherein said carboxylate used in the neutralising step is an alkali metal acetate.

12. A process according to claim 11, wherein said alkali metal acetate is sodium acetate.

13. A process according to claim 7, wherein the neutralisation reaction is carried out at the lowest possible temperature whereby the solvent is still in liquid form.

* * * * *